United States Patent [19]
Inada et al.

[11] 3,953,528
[45] Apr. 27, 1976

[54] PROCESS FOR SUBLIMATION PURIFICATION OF CRUDE HYDROQUINONE WITH STIRRED AND FLUIDIZED BED

[75] Inventors: Kazutoshi Inada, Minami-ashigara; Masatoshi Sugiyama; Yasuo Nishigaki, both of Odawara; Sugihiko Tada, Minami-ashigara, all of Japan

[73] Assignee: Fuji Photo Film Co., Ltd., Minami-ashigara, Japan

[22] Filed: Sept. 14, 1973

[21] Appl. No.: 397,472

[30]  Foreign Application Priority Data
 Sept. 14, 1972  Japan................................47-92503

[52] U.S. Cl............................ 260/621 A; 23/294 R; 203/49
[51] Int. Cl.²................... C07C 37/22; C07C 37/38
[58] Field of Search.................. 260/621 A; 23/294

[56]  References Cited
 UNITED STATES PATENTS

| | | | |
|---|---|---|---|
| 1,446,551 | 2/1923 | Dissosway........................ | 260/621 A |
| 1,446,564 | 2/1923 | Jackson.......................... | 260/621 A |
| 3,834,997 | 9/1974 | Hocking et al...................... | 23/294 |

OTHER PUBLICATIONS

Kirk–Othmer, "Ency. of Chem. Tech.," Vol. 11, p. 483, (1967).
Perry et al., "Chemical Eng. Hand.," pp. 20–51–53, (1963).
Perry et al., "Chem. Eng. Hand.," pp. 17–23–26, (1963).

*Primary Examiner*—Norman Morgenstern
*Attorney, Agent, or Firm*—Sughrue, Rothwell, Mion, Zinn and Macpeak

[57]  ABSTRACT

Crude hydroquinone containing impurities is purified in a sublimation purification apparatus where the crude hydroquinone is introduced into a stirred and fluidized bed, a carrier gas which is inert to the hydroquinone is passed therethrough, and the temperature therein is kept at about 110°–170°C whereby crude hydroquinone is sublimed, and thereafter a mixed gas consisting of the sublimed vapor and the carrier gas is introduced into a condenser at a temperature at about 25°–90°C whereby the hydroquinone only is fractionally solidified. After the sublimation purification, hydroquinone of high purity can be collected.

15 Claims, 1 Drawing Figure

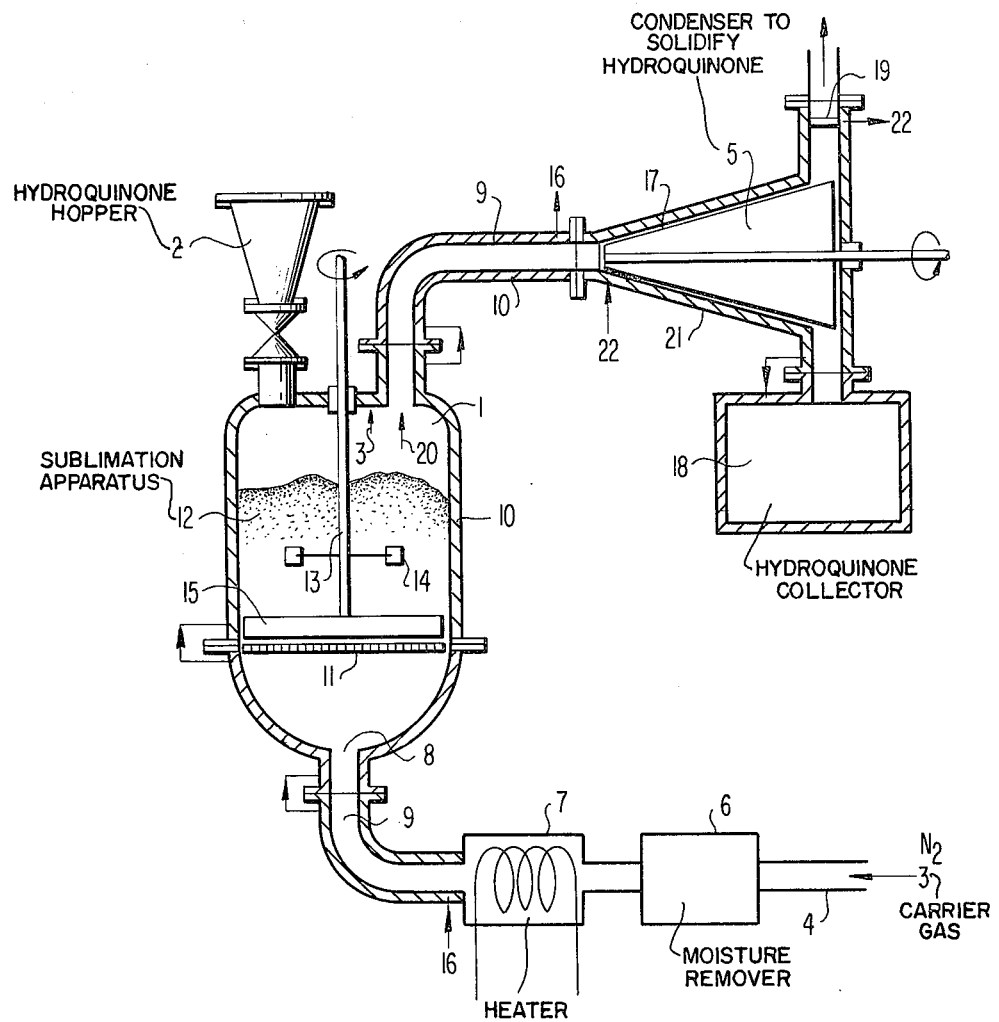

PROCESS FOR SUBLIMATION PURIFICATION OF CRUDE HYDROQUINONE WITH STIRRED AND FLUIDIZED BED

BACKGROUND OF THE INVENTION

1. Field of the Invention

The present invention relates to a process for purifying crude hydroquinone containing impurities by subliming the crude hydroquinone with an apparatus having a stirred and fluidized bed and then collecting only the hydroquinone which has been fractionally solidified in a condenser.

2. Description of the Prior Art

In general, the hydroquinone used in photo-chemical industries requires high purity. Crude hydroquinone prepared according to a process as described in U.S. Pat. No. 2,715,646 and British Patent No. 641,250 for the liquid phase oxidation of para-diisopropyl-benzene contains about 10% of inorganic salts as well as traces of several tens of different kind of impurities, and it is known that these trace impurities cause some coloration which is harmful to the quality of the product and that some impurities additionally deleteriously affect photographic characteristics.

When attempts are made to completely remove these trace impurities using an extraction process, an adsorption process or the like separation process, such processes are too expensive, and therefore they are unsuitable industrially. On the other hand, a separation using a distillation also is unsuitable for the purification of hydroquinone in that the hydroquinone is easily oxidized in the distillation process and that hydroquinone reacts with the existing trace impurities therein and polymerizes or changes into other substances.

SUMMARY OF THE INVENTION

An object of the present invention is to eliminate the above described drawbacks in the prior art, and more precisely, to obtain purified hydroquinone crystals of high photographic purity, in a high yield and at a low expense, from a crude hydroquinone using a sublimation process, without deteriorating the quality of the resulting hydroquinone itself.

BRIEF EXPLANATION OF THE ACCOMPANYING DRAWING

The FIGURE shows a flow sheet of a sublimation purification process using equipment providing a stirred and fluidized, according to one embodiment of the present invention.

DETAILED DESCRIPTION OF THE INVENTION

It is generally known that, when only the desired material to be purified is sublimable and the other impurities are not sublimable, a purification process using sublimation is advantageous for the purification of the sublimable material, in addition to the case of hydroquinone. However, the crude hydroquinone prepared by the liquid phase oxidation of para-diisopropyl-benzene contains sublimable impurities, and therefore, conventional sublimation process, for example, as described in French Pat. No. 2,043,368 and British Patent No. 1,275,232 are unsuitable for attaining a sufficient purity for the hydroquinone purified by sublimation. The present inventors have tried various experiments on sublimation purification methods for crude hydroquinone containing sublimable substances other than hydroquinone, and at last have achieved the following result:

1. Using an entrainer sublimation process in which a carrier gas is passed.
2. The carrier gas used must be inert to the hydroquinone.
3. A normal pressure operation is better than a reduced pressure operation.
4. The temperature of operation is preferably in the range of about 110°–170°C.
5. A stirred and fluidized bed is the most suitable type for the sublimation apparatus.

As a sublimation process, a simple sublimation type can be considered in which a solid is heated and sublimed and thereafter the thus sublimed vapor only is transported to a condenser. This type of sublimation process, however, is unsuitable for the sublimation of hydroquinone, since heat transfer is insufficient as compared with the use of a carrier gas, and further, it is necessary to elevate the temperature of operation. In addition, this type of process is additionally defective in that the sublimed vapor sometimes solidifies in transport pipes connected to the condenser thereby clogging the pipes. In view of these points, the above described entrainer sublimation approach where a carrier gas is passed through the sublimation apparatus is the most advantageous approach for the sublimation process of the present invention.

The primary role of the carrier gas is to improve the heat transfer in the apparatus and to smoothly transport the sublimed vapor to the condenser. Therefore, all gases which are inert to hydroquinone such as nitrogen, helium, neon, argon, and the like can be employed as the carrier gas.

The pressure of operation is most suitably normal pressures, e.g., about 680–880 mmHg, preferably about 750–770 mmHg. In general, when all the other operation conditions are same, the lower the operation pressure is, the higher the sublimation speed. However, when the crude hydroquinone contains sublimable materials other than hydroquinone itself, the other trace impurities than hydroquinone also sublime under reduced pressure operation, and thus the purity of the resulting hydroquinone is lowered, which is a fatal defect. The present inventors have overcome this problem by performing the sublimation process under normal pressure. Although the sublimation of the impurities is not nonexistent even under the normal pressure operation, the amount of sublimed impurities at normal pressure is far less than that obtained under a reduced pressure, and the sublimed impurities can be separated substantially completely from hydroquinone in a later fractional collection (as disclosed in Japanese Patent Publication Nos. 11324/67 and 27729/68, and using conventional techniques as disclosed in John H. Perry "Chemical Engineer's Handbook," 4th Ed. McGraw-Hill page 17–23). Heat transfer results from a contact between the carrier gas and the hydroquinone, and so, if the operation is carried out under a reduced pressure, the carrier gas is rarefied and heat transfer becomes insufficient. In view of such, it is not advantageous to carry out the present invention at a reduced pressure. Moreover, a reduced pressure operation is inferior to the normal pressure operation from the standpoint of construction of the apparatus, operation of the process such as scale up, cost and like.

In general, sublimation is preferably performed at as high a temperature as possible, since the rate of sublimation is higher with higher temperatures. However with respect to the sublimation of hydroquinone, the melting point of the hydroquinone is about 170°C, and therefore when the temperature of operation approaches the melting point, the hydroquinone begins to melt and the area for heat transfer becomes too small at last thereby markedly decreasing heat transfer. For this reason, the temperature in the sublimation of hydroquinone should be such that the hydroquinone is solid, e.g., about 170°C or below. The lower limit of the operation temperatures is not so limited as above, but is preferably about 110°C from the standpoint of sublimation rate. Industrally, the temperature of operation is preferably in the range of about 140° to 160°C or so.

The sublimation apparatus is preferably one in which the temperature of operation can be easily controlled and a high sublimation rate can be achieved. With respect to the heat treatment in the sublimation apparatus, it is necessary to take appropriate steps so that the crude hydroquinone treated is not locally and excessively heated elevating the temperature of the hydroquinone over the melting point thereof. In order to achieve these conditions, a fluidized bed is the best type where a carrier gas is passed therethrough. More particularly, a fluidized bed is especially advantageous in that, when the bed is used it is easy to keep the temperature of operation uniform, and further, since the solid hydroquinone is fluidized, the contacting area between the fluidized hydroquinone and the carrier gas is increased and thus the heat transfer therebetween is improved and a high sublimation rate can be attained. In view of these points, a process using a fluidized bed is far superior to any other processes using a gasification coil or the like. However, since the hydroquinone consists of needle-like crystals, the mere blowing of the carrier gas into the fluidized bed is insufficient. This is because disadvantageously channelling or the like often occurs during the blowing of the carrier gas and it is difficult to obtain a stable fluidized bed. It is necessary to appropriately stir the fluidized bed so as to eliminate these drawbacks and to obtain a stable fluidized bed. Therefore, a stirred and fluidized bed is most suitable for the sublimation apparatus.

With respect to the carrier gas, all gases such as those described hereinbefore which are inert to hydroquinone can be employed. For example, nitrogen gas is especially suitable in the present invention.

It is a matter of course that the purification method of the present invention can well apply not only to the purification of the crude hydroquinone prepared from para-diisopropyl-benzene but also to the purification of any other crude hydroquinone prepared by other production methods, for example by the well known aniline method.

The present process also can be applied to the purification of any other type of crude hydroquinone containing no sublimable impurities.

Now, the present invention will be explained more specifically be reference to the drawing attached hereto, so as to easily understand the present invention.

The FIGURE shows a flow sheet of a sublimation purification process using a stirred and fluidized bed apparatus of the present invention. In the FIGURE, various controlling devices and attendant equipment are not shown, since these are well known to one of skill in this art.

Crude hydroquinone, after being subjected to solvent removal, is dried to form a powder, and an appropriate amount of the resulting powder is fed in a stirred and fluidized bed sublimation apparatus 1 via a hopper 2. The particle size generally used is a diameter of from about 0.2–0.7 mm$\phi$ for a length of about 1.5 mm and from about 0.04–0.2 mm $\phi$ for a length of about 1.5 mm. On the other hand, a carrier gas 3 is fed via a duct 4. The carrier gas 3 is, as mentioned above, one which is inert to hydroquinone at the sublimation point thereof, and further is one which remains gaseous in a condenser 5. Nitrogen gas is a preferred carrier gas. The flow rate of the gas generally depends on the cross sectional area of the fluidized bed and the amount of hydroquinone to be purified. Establishment of a stable fluidized bed generally is all that is required and such can be obtained, for example, using a flow rate of about 10–15 liter/m for a fluidized bed diameter of about 10 cm.

Since hydroquinone is easily oxidized in the presence of moisture, the moisture present in the carrier gas is removed in a moisture removing device 6. This removal is carried out using adsorption or other thermodynamic methods. In case of the nitrogen gas, for example, calcium chloride, silica gel or the like can be used. Desirably the carrier gas will be dried to the extent of no more than about 0.5 percent by weight moisture.

The carrier gas 3 free from moisture is transported to a heating device 7 and is heated up to the sublimation temperature.

The carrier gas 3 heated up to the sublimation temperature is fed into the stirred and fluidized bed sublimation device 1 via an inlet 8. The sublimation device 1 and a pipe line 9 are jacketed with jacket 10 and are kept at a sublimation temperature using an appropriate heat transfer medium 16 such as dephenyls, napthalene and the like.

The carrier gas 3 introduced into the sublimation apparatus thereafter passes through a porous plate 11 having a mesh smaller than the hydroquinone particle size, i.e., less than 0.11 mm in diameter for dispersion, and the gas fluidizes the crude hydroquinone particles 12.

On the other hand, the interior of the sublimation device is constantly stirred so as to increase the efficiency of fluidization and to prevent any channelling. The agitator is composed of a motor having a reduction gear (not shown), a shaft 13 and one or more stirring blades 14, 15. At least one of the blades 14, 15 in the lowest position is an oar-blade 15, which is set closest to the porous plate 11. The oar-blade 15 is effective for fluidization of hydroquinone particles and for prevention of any cake formation. The rate of stirring or agitation is not critical but it should desirably be not so low that cake formation is permitted nor so high that the particles are pulverized.

A sublimed vapor 20 is transported to the condenser 5 together with the carrier gas 3, where the vapor 20 is solidified. When the sublimed vapor consists of not only hydroquinone but also other impurities, it is necessary to control the temperature of the condenser 5 is an appropriate range. The present inventors have found that, when the temperature of the condenser 5 is in the range of about 25°–90°C, almost all of the hydroquinone is solidified while the trace impurities are not. After the hydroquinone only is fractionally solidified, the remaining gaseous materials consisting of impurities and the carrier gas 3 are removed via a porous plate 19. If, on the contrary, the temperature in the condenser 5 is lower than the above described range, some impurities also solidify together with hydroquinone to impart a yellowish coloring to the purified hydroquinone. Therefore, a lower temperature is unsuitable. The temperature range for the fractional solidification varies, depending upon the properties of the impurities contained in the crude hydroquinone, and therefore, the above described temperature range does not always apply to the purification of crude hydroquinone prepared using other manufacturing processes. For example, when the crude hydroquinone is prepared from aniline according to the so-called aniline process, the sublimable substance contained in the resulting crude product is hydroquinone only, and therefore, the lower limit of the temperature in the condenser 5 can be broadened further and lower temperatures used. In order to hold the temperature of the condenser 5 in an appropriate range, an appropriate coolant 22 is passed through jacket 21.

Hydroquinone solidifies not only within the space in the condenser, but also on the wall of the condenser 5. The hydroquinone solidified on the wall of the condenser is scraped together with a scraper 17 and is collected in a stock part 18. The space between the scraper 17 and the wall of the condenser 5 is preferably as small as possible, in order to prevent the adherence of or build up of a large amount of purified hydroquinone crystals.

The present invention will be explained in greater detail by reference to the following Examples, in order to further specifically set forth the effect of the present invention. Unless otherwise indicated, all parts and percents are by weight.

EXAMPLE 1

50 g of commercial hydroquinone for photographic use prepared using the aniline process was fed into a stirred and fluidized bed apparatus as described in the FIGURE, and the sublimation temperature was set at 135°C. Nitrogen gas was used as the carrier gas, and after the moisture present therein was removed using calcium chloride and silica gel, the resulting nitrogen gas was heated to the sublimation temperature and then was introduced into the sublimation apparatus at a flow rate of 10 liters/min. The speed of the stirrer was set at 60 r.p.m. The temperature of the condenser was set at 40°–50°C, and all of the equipment was run for 1 hour. After analysis of the solidified product using gas chromatography (SE-30, which is methyl siloxane, a product of Gaschlo Kogyo K. K., was used as the column material and nitrogen gas as the carrier gas), it was confirmed that about 100 percent pure hydroquinone free from any residue was collected in the condenser.

EXAMPLE 2

50 g of crude hydroquinone particles prepared by the liquid phase oxidation of para-diisopropyl-benzene were fed into the same apparatus as described in Example 1, where the particles were sublimed and purified. After the analysis of the crude hydroquinone used employing gas chromatography, it was noticed that 8% inorganic salts such as Glauber's salt, etc. as well as other several ten kinds of impurities such as dihydroxyacetophenone, etc. were contained therein and that the color thereof was yellowish-brown. The conditions of operation were the same as those used in the Example 1.

After running for 1 hour, pure white crystals of purified hydroquinone were obtained, and after analysis of the resulting crystals using gas chromatography, no impurities were observed.

The residues, analyzed with gas chromatography, contained the same amount of inorganic salts such as Glauber's salt, etc. as before the sublimation, about 5% hydroquinone and several kinds of impurities. The recovery yield of the hydroquinone in this step is 95 percent, while it is difficult to attain such high yield and purity using any other adsorption or extraction technique, even repeating such several times.

The conditions for analysis for the gas chromatography used for the analysis of the raw material and the purified product were the same as those employed in Example 1.

EXAMPLE 3

50 g of crude hydroquinone particles prepared as described in Example 2 were fed into the same apparatus as described in Example 1, where the particles were sublimed and purified. The conditions of operation were as follows: The temperature in the sublimation apparatus was kept at 135°C, and the temperature in the condenser at 40°–50°C. The pressure of operation was a reduced pressure of 1-2 mmHg. No carrier gas was used and no agitation was employed. After running the equipment for 1 hour and then analyzing the resulting product using gas chromatography, about 70% hydroquinone was collected, which was, however, somewhat yellow in color. Thus, when sublimation was carried out under a reduced pressure, the purity of the resulting hydroquinone is lowered since the sublimation rate is low and further some materials, which do not sublime in normal pressure operation, sublime together with the hydroquinone. The conditions of operation of the gas chromatography used for analysis were quite the same as the Example 1.

EXAMPLE 4

Crude hydroquinone prepared from para-diisopropyl-benzene by the liquid phase oxidation thereof followed by solvent (acetone) removal by distillation was fed into the same apparatus as described in Example 1, and then was sublimed and purified under the same conditions as described in Example 1. Apart from this, the crude hydroquinone used in the above purification was further subjected to extraction purification with ethylene dichloride to prepare purified hydroquinone. The resulting purified hydroquinone was also fed into the same apparatus as described in Example 1, and then was sublimed and purified also under the same conditions as described in Example 1. In each case, the amount of hydroquinone fed into the apparatus was 20 g. The results obtained from these experiments are shown in Table 1. On analysis of the hydroquinone solidified in the condenser part using gas chromatography, no impurity was found in each case. As shown in Table 1, the recovery yield of the purified hydroquinone was 95 percent or more in each case, and it is can be seen that the effect of the purification step of the present invention is always high, almost irrespective of the performance of extraction before the purification process of the present invention.

Table 1

|  | Content of Hydroquinone before Sublimation | Yield of Hydroquinone after Sublimation |
|---|---|---|
| Before Extraction | 88.0% | 95.5% |
| Before Extraction | 88.0% | 96.5% |
| After Extraction | 82.0% | 99.1% |
| After Extraction | 82.8% | 95.0% |

The advantages of the present invention are as follows:

1. Hydroquinone having high photographic purity can be obtained in a higher yield and at a lower cost than with any other extraction or adsorption purification process.

2. The effect of the purification according to the present invention is high, regardless of the degree of preextraction purification, and therefore, any extraction purification step can be omitted, and hydroquinone of photographic purity can be obtained utilizing only the sublimation purification step of the present invention. Accordingly, the present invention is advantageous from the standpoint of expense and of prevention of pollution since no solvents are employed.

While the invention has been described in detail and with reference to specific embodiments thereof, it will be apparent to one skilled in the art that various changes and modifications can be made therein without departing from the spirit and scope thereof.

What is claimed is:

1. A process for purifying hydroquinone comprising introducing crude hydroquinone prepared using the aniline process containing impurities into a stirred and fluidized bed, passing a dried carrier gas which contains no more than about 0.5% by weight moisture and which is inert to the hydroquinone through said bed, and holding the temperature in said bed at about 110° to 170°C and the pressure at from 680 to 880 mmHg, which temperature is below the melting point of hydroquinone, whereby the crude hydroquinone is sublimed, and thereafter introducing a gaseous mixture of said carrier gas and sublimed vapor into a condenser at a temperature of about 25° to 90°C whereby the hydroquinone only is solidified from said gaseous mixture.

2. The process as claimed in claim 1, wherein said sublimation is carried out at normal pressure.

3. The process as claimed in claim 1, wherein said carrier gas is nitrogen gas.

4. The process as claimed in claim 1, wherein said sublimation is conducted at a temperature of from 140° to 160°C.

5. The process as claimed in claim 1, wherein crude hydroquinone contains sublimable impurities.

6. The process as claimed in claim 5, wherein said sublimable impurities sublime in an amount at normal pressure substantially less in the amount of sublimation of such impurities at reduced pressure.

7. The process as claimed in claim 1, wherein said crude hydroquinone is free of sublimable impurities.

8. A process for purifying hydroquinone comprising introducing crude hydroquinone containing impurities into a stirred and fluidized bed, said crude hydroquinone having been prepared by the acid catalyzed decomposition of p-diisopropylbenzenedihydroperoxide obtained from the air oxidation of p-diisopropylbenzene, passing a dried carrier gas which contains no more than about 0.5% by weight moisture and which is inert to the hydroquinone through said bed, and holding the temperature in said bed at about 110° to 170°C and the pressure at from 680 to 880 mmHg, which temperature is below the melting point of hydroquinone, whereby the crude hydroquinone is sublimed, and thereafter introducing a gaseous mixture of said carrier gas and sublimed vapor into a condenser at a temperature of about 25° to 90°C whereby the hydroquinone only is solidified from said gaseous mixture.

9. The process of claim 8, wherein said crude hydroquinone has been subjected to solvent removal by distillation prior to said purifying.

10. The process of claim 8, wherein said sublimation is carried out at normal pressure.

11. The process of claim 8, wherein said carrier gas is nitrogen gas.

12. The process of claim 8, wherein said sublimation is conducted at a temperature of from 140° to 160°C.

13. The process of claim 8, wherein said crude hydroquinone contains sublimable impurities.

14. The process of claim 13, wherein said sublimable impurities sublime in an amount at normal pressure substantially less in the amount of sublimation of such impurities at reduced pressure.

15. The process of claim 8, wherein said crude hydroquinone is free of sublimable impurities.

* * * * *